US006800448B2

(12) United States Patent
Rider et al.

(10) Patent No.: US 6,800,448 B2
(45) Date of Patent: Oct. 5, 2004

(54) OPTOELECTRONIC SENSOR

(75) Inventors: Todd H. Rider, Acton, MA (US); Laura Smith, Carlisle, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 353 days.

(21) Appl. No.: 09/848,811

(22) Filed: May 4, 2001

(65) Prior Publication Data

US 2001/0016328 A1 Aug. 23, 2001

Related U.S. Application Data

(63) Continuation of application No. 09/169,196, filed on Oct. 9, 1998, now Pat. No. 6,248,542, which is a continuation-in-part of application No. 08/987,410, filed on Dec. 9, 1997, now Pat. No. 6,087,114.

(51) Int. Cl.[7] .............................................. G01N 33/50
(52) U.S. Cl. .................... 435/7.2; 385/12; 385/129; 422/55; 422/58; 422/82.5; 422/82.06; 422/82.07; 422/82.08; 422/82.09; 422/82.11; 435/7.21; 435/287.1; 435/287.2; 435/288.7; 435/808; 436/164; 436/172; 436/518; 436/519; 436/527; 436/536; 436/805

(58) Field of Search ...................... 385/12, 129; 422/55, 422/58, 82.05, 82.06, 82.07, 82.08, 82.09, 82.11; 435/7.2, 7.21, 287.1, 287.2, 288.7, 808; 436/164, 172, 518, 527, 536, 805, 519

(56) References Cited

U.S. PATENT DOCUMENTS 6,087,114 A * 7/2000 Rider ........................... 422/58
6,248,542 B1 * 6/2001 Rider et al. .................... 422/58

* cited by examiner

Primary Examiner—Christopher L. Chin
(74) Attorney, Agent, or Firm—Hamilton, Brook, Smith & Reynolds, P.C.

(57) ABSTRACT

A device for detecting the presence of an antigen including (1) a cell having antibodies which are expressed on the surface of the cell and are specific for the antigen to be detected, where binding of the antigen to the antibodies results in an increase in calcium concentration in the cytosol of the cell, the cell further having a emitter molecule which, in response to the increased calcium concentration in the cytosol, emits a photon; (2) a liquid medium for receiving the antigen and in which the cell is immersed; and (3) an optical detector arranged for receiving the photon emitted from the cell.

13 Claims, 2 Drawing Sheets

OPTOELECTRONIC SENSOR

This application is a continuation of U.S. application Ser. No. 09/169,196, filed Oct. 9, 1998, now U.S. Pat. No. 6,248,542, which is a continuation-in-part of U.S. application Ser. No. 08/987,410, filed Dec. 9, 1997, now U.S. Pat. No. 6,087,114. Both parent applications are hereby incorporated by reference in their entirety.

BACKGROUND OF THE INVENTION

The need for small, fast, and sensitive detectors of biological agents which are able to continuously monitor an environment for extended periods of time is underscored by the proliferation of biological and chemical weapons, the poor man's nuclear weapon. Under battlefield conditions, a useful detector would rapidly alert a soldier when a specific biological or chemical agent is detected so that countermeasures can quickly be implemented.

Such detectors would be useful in non-military applications as well. Rapid detection of antibiotic-resistant bacteria in a patient would help clinicians select a more effective therapeutic regimen. Continuous monitoring of a city's drinking water supply would provide early warning of potential pathogens, giving public works officials more time to manage the potential health risks to the public. In addition, the use of these detectors in meat and poultry inspections would be a significant improvement over the current "poke-and-smell" procedure.

All vertebrates acquire a specific immune response to a foreign agent (antigen) in part by generating an immense diversity of antibody molecules. Antibody molecules bind to antigen with high specificity, e.g., they can differentially bind to two closely related strains of bacteria or viruses.

Antibodies are produced by B cells, a crucial component of the immune system. An antigen can activate a B cell by binding to antibodies on its surface, leading to a cascade of intracellular biochemical reactions which causes a calcium ion influx into the cytosol of the B cell.

For a review of antibody structure and function and B cell activation, see Paul, editor, *Fundamental Immunology*, 3rd ed., Raven Press, New York (1993).

SUMMARY OF THE INVENTION

This invention relates to a device for detecting an antigen. The device includes a liquid medium containing cells (e.g., a B cell or fibroblast) and an optical detector, the liquid medium receiving the antigen. Each of the cells has antibodies (e.g., chimeric or single chain antibodies) which are expressed on its surface and are specific for the antigen to be detected. Binding of the antigen to the antibodies results in an increase in calcium concentration. The cells also contain emitter molecules (e.g., aequorin or indo-1) in their cytosol which emit photons in response to the increased calcium concentration in the cytosol. The detector can be separated from the medium containing the cells by a covering (e.g., glass) that is transparent to the photons. Such a covering can serve to support the medium, protect a fragile surface of the detector, or be used as a lens. The optical detector, e.g., a charge-coupled device (CCD) is able to detect the photons emitted from the cells in response to the increased calcium concentration and indicate to the user that the antigen to be detected is present. Other optical detectors which can be used in the device include a photomultiplier tube or a photodiode. In some embodiments, the optical detector is able to distinguish individual cells.

The device can be contained within a housing made from, for example, aluminum, plastic, or stainless steel. Such a housing can prevent contamination of the device with extraneous organisms. The housing can include two halves attached to each other on one side of the housing by a hinge joint. In applications where an airborne antigen is to be detected, the housing can contain one or more openings for the antigen to pass into the device. Such an opening can be screened by an antigen-permeable barrier such as a metal mesh or a membrane.

The sample containing the antigen can pass through a filter before the antigen contacts the cells. Suitable filters include passive filters (e.g., filter with determined pore sizes, affinity columns or immunofilters) and active filters (e.g., fluorescence-activated sorters, active size sorters, or microfluidic systems).

The invention also features a method for detecting the presence of an antigen, which includes providing a sample (e.g., a volume of air) suspected of containing the antigen; introducing the sample into a device containing cells immersed in a medium; and monitoring photon emission as an indication of whether the antigen is present. The cells used in this method are described above.

Further, the invention includes a cell containing an emitter molecule and having antibodies on its surface, so as to be useful in the devices and methods of the invention.

Other features or advantages of the present invention will be apparent from the following drawings, detailed description, and the claims. Any publications cited in this disclosure are hereby incorporated by reference.

DETAILED DESCRIPTION

Figure 1:
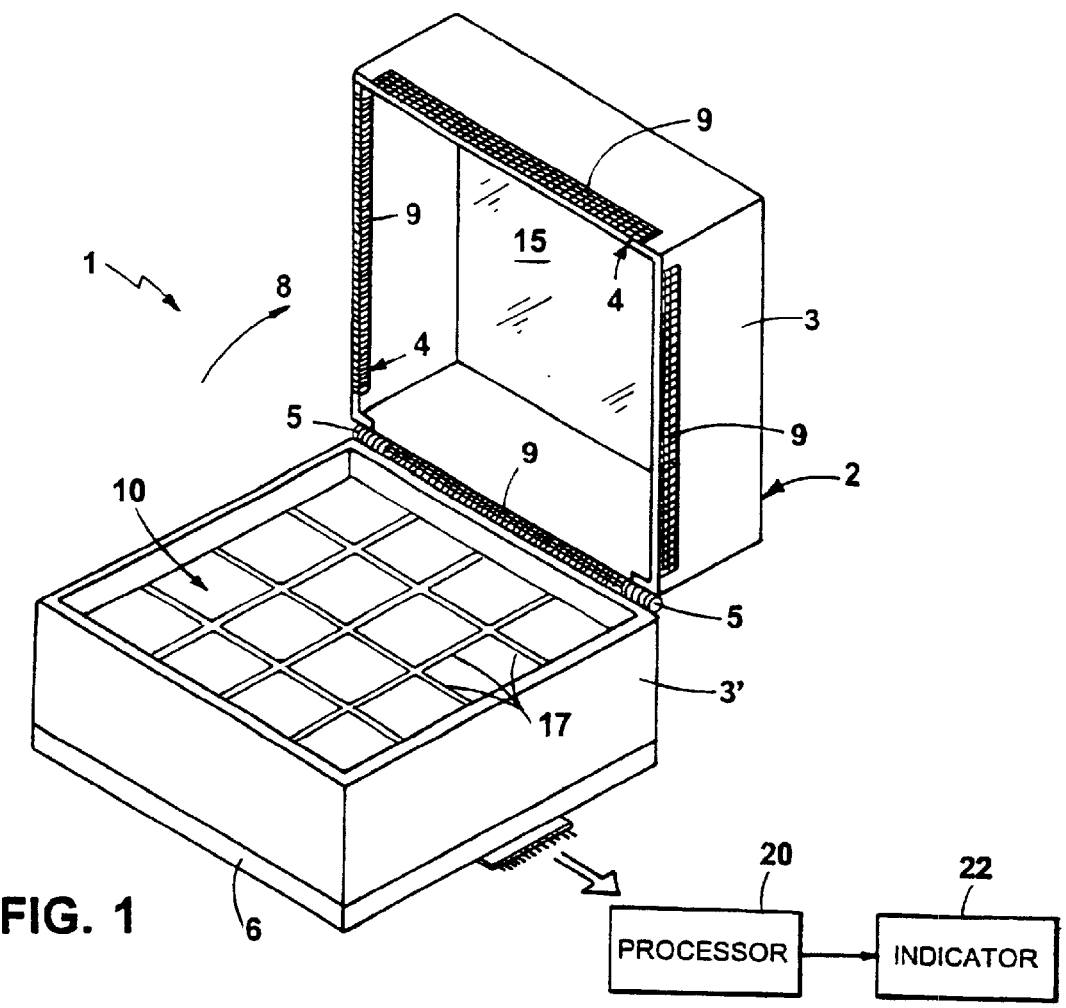
FIG. 1 is perspective view of a device for detecting an antigen in its open position.

The invention is based on the discovery that cells having antibodies on its surface and containing a compound that emits a photon upon external stimulation by an antigen can be used in an optoelectronic sensor. The biological aspect of the invention are discussed below.

I. Cells

The cell which has surface-bound antibodies can be either prokaryotic or eukaryotic. Upon binding of antigen to the antibodies, the cell mobilizes calcium ions into the cytosol. An example of a cell useful in the device and methods of the invention is a B cell (i.e., a B cell from a cold or warm-blooded vertebrate having a bony jaw) which can be genetically engineered to express one or more surface-bound monoclonal antibodies. It also can be produced by, for example, immunizing an animal with the antigen to be detected and harvesting the B cell from the immunized animal. The harvested B cells can be further immortalized and screened for production of a surface monoclonal antibody specific for the antigen to be detected.

Alternatively, the cell can be a fibroblast, which offers the advantage that the cell can be adhered to a substrate of a device of the invention. However, fibroblasts do not contain the signal transduction machinery necessary to transfer a signal from the cytoplasmic portion of a surface antibody to calcium stores in the cell. To overcome this problem, a chimeric surface antibody can be expressed in the fibroblast. This chimeric antibody contains a cytoplasmic amino acid sequence derived from a polypeptide (e.g., a fibroblast growth factor receptor) that can transduce a signal from the inner surface of the plasma membrane of the fibroblast to intracellular calcium stores. Thus, when an antigen binds to the extracellular portion of the chimeric antibody to cause antibody aggregation on the surface, calcium mobilization is induced. A similar strategy using chimeric antibodies can be employed for any other cell type which is not a B cell, so that the cell is suitable for use in the devices and methods of the invention.

Growth of the cell can be controlled by any means well known in the art, including providing anti-mitotic drugs (e.g., α-amanitin) or growth factors (e.g., fetal bovine serum) in the medium. Alternatively, cells can be genetically engineered to grow at a determined rate. As discussed above, any cell can be used as long as binding of the antigen to the antibodies on the surface of the cell leads to an increase in calcium concentration in the cytosol. In fact, the cell can be a non-living, manufactured unit as long as it satisfies the above requirement.

II. Antibodies

An antibody which specifically binds to the antigen to be detected is a molecule which binds to the antigen or a epitope of the antigen, but does not substantially bind other antigens or epitopes in the sample. Such antibodies can be chimeric (i.e., contain non-antibody amino acid sequences) or single chain (i.e., the complementarity determining region of the antibody is formed by one continuous polypeptide sequence).

Polyclonal cells expressing antibodies can be prepared by immunizing a suitable animal with the antigen to be detected. The cells producing antibody molecules directed against the antigen can be isolated from the animal (e.g., from the blood) and further purified by well-known techniques, such as panning against an antigen-coated petri dish.

Alternatively, surface antibody-producing cells can be obtained from the animal and used to prepare a monoclonal population of cells producing surface antibodies by standard techniques, such as the hybridoma technique originally described by Kohler et al., Nature 256:495–497 (1975); Kozbor et al., Immunol Today 4:72 (1983); or Cole et al., *Monoclonal Antibodies and Cancer Therapy*, Alan R. Liss Inc., pp. 77–96 (1985). The technology for producing cells expressing monoclonal antibodies is well known (see, e.g., *Current Protocols in Immunology* (1994) Coligan et al. (eds.) John Wiley & Sons, Inc., New York, N.Y.), with modifications necessary to select for surface antibodies rather than secreted antibodies.

Any of the many well known protocols used for fusing lymphocytes and immortalized cell lines can be applied for the purpose of generating a cell producing a surface monoclonal antibody (see, e.g., *Current Protocols in Immunology*, supra; Galfre et al., Nature 266:55052, 1977; Kenneth, In *Monoclonal Antibodies: A New Dimension In Biological Analyses*, Plenum Publishing Corp., New York, N.Y., 1980; and Lerner, Yale J Biol Med 54:387–402 (1981). Moreover, the ordinarily skilled worker will appreciate that there are many variations of such methods which also would be useful.

As an alternative to preparing monoclonal cells, a nucleic acid encoding a monoclonal antibody can be identified and isolated by screening a recombinant combinatorial immunoglobulin library (e.g., an antibody phage display library) with the antigen to thereby isolate immunoglobulin library members that bind the antigen. Kits for generating and screening phage display libraries are commercially available (e.g., the Pharmacia *Recombinant Phage Antibody System*, Catalog No. 27-9400-01; and the Stratagene *SurfZAP*™ *Phage Display Kit*, Catalog No. 240612). Additionally, examples of methods and reagents particularly amenable for use in generating and screening antibody display library can be found in, for example, U.S. Pat. No. 5,223,409; PCT Publication No. WO 92/18619; PCT Publication No. WO 91/17271; PCT Publication WO 92/20791; PCT Publication No. WO 92/15679; PCT Publication WO 93/01288; PCT Publication No. WO 92/01047; PCT Publication No. WO 92/09690; PCT Publication No. WO 90/02809; Fuchs et al., Bio/Technology 9:1370–1372 (1991); Hay et al., Hum Antibod Hybridomas 3:81–85 (1992); Huse et al., Science 246:1275–1281 (1989); Griffiths et al., EMBO J 12:725–734 (1993).

After the desired member of the library is identified, the specific sequence can be cloned into any suitable nucleic acid expresser and transfected into a cell such as a fibroblast. The expresser can also encode amino acids operably linked to the antibody sequence as appropriate for the cell which is to express the antibody. As discussed above, the cytoplasmic transmembrane sequence of a fibroblast growth factor receptor can be linked to a single-chain antibody specific for the antigen to be detected, so that the cell immobilizes calcium when contacted with the antigen. Although separate recombinant heavy chains and light chains can be expressed in the fibroblasts to form the chimeric antibody, single chain antibodies also are suitable (see, e.g., Bird et al., Trends Biotechnol 9:132–137, 1991; and Huston et al., Int Rev Immunol 10:195–217, 1993).

III. Photon Emitter Molecules

A suitable emitter molecule is any molecule that will emit a photon in response to elevated cytosolic calcium concentrations, including bioluminescent and fluorescent molecules. One emitter molecule, the bioluminescent aequorin protein, is described in Button et al., Cell Calcium 14:663–671 (1993); Shimomura et al., Cell Calcium 14:373–378 (1993); and Shimomura, Nature 227:1356–1357 (1970). Aequorin generates photons by oxidizing coelenterazine, a small chemical molecule. Coelenterazine diffuses through cellular membranes, so coelenterazine or an analog thereof can be added to the culture medium surrounding the cells. Alternatively, genes encoding enzymes that make coelenterazine can be introduced into the cells. In another embodiment, bioluminescent green fluorescent protein (GFP) can be used (see Chalfie, Photochem Photobiol 62:651–656 [1995]). In this embodiment, the cell cytosol contains both GFP and aequorin. In response to elevated calcium in the cytosol, aequorin donates energy to GFP in an emissionless energy transfer process. GFP then emits the photon. Alternatively, the emitter molecule can be a calcium-sensitive fluorescent molecule (e.g., indo-1) which is illuminated by a wavelength of light suitable to induce fluorescence.

Aequorin, or any other emitter molecule, can be introduced into the cell by methods well know in the art. If the emitter molecule is a protein (as is the case with aequorin), the cell can contain an expression vector encoding the protein (i.e., a nucleic acid or virus which will produce the emitter molecule when introduced into a cell). An expression vector can exist extrachromosomally or integrated into the cell genome.

IV. Detection of One or More Antigens

The antigen can be introduced into the device passively. For example, airborne anthrax bacteria can enter the device through an opening via air currents. Alternatively, an airborne antigen can be actively introduced into the device by, e.g., a fan. The antigen to be detected can also reside in an aqueous medium. For example, a drop of the aqueous sample can be added to the medium containing the cells.

Instead of grouping cells in sectors within an array, the cells specific for different antigens can be interspersed if the photon emitted from a cell specific for one antigen is of a wavelength different from the photon emitted from a cell specific for another antigen. In such a situation, the optical detector can differentially detect the photons of different wavelengths. For example, cells sensitive to different antigens can contain different aequorin-like proteins and/or different fluorescent proteins so that the different cells could be distinguished on the basis of differing photon emission characteristics (e.g., peak wavelength, spectral width of emission, or decay rate). To allow identification of a larger number of antigens, signal multiplexing can also be used. For example, the emission spectrum of a given type of cell could have multiple identifiable peaks. Different fusion proteins (e.g., aequorin and a fluorescent protein joined together by fusing their genes in frame) could be useful for this purpose.

In general, multivalent antigens (which contain multiple binding sites for a specific antibody) are required to cross-link surface antibodies on the cell in order to trigger calcium influx into the cytosol. However, monovalent antigens (which contain only one binding site for a specific antibody) can also be detected by the device. Such antigens can be detected if several monovalent antigens are linked together (by noncovalent bonding, for example) as the antigens bind to the antibodies on the surface of the cell. Alternatively, the cell can be genetically engineered to expressed two or more antibodies which are specific to the same antigen but bind to spatially separated epitopes of the antigen, thereby allowing a single antigen to bind to at least two antibodies on the cell surface with different specificities.

Without further elaboration, it is believed that one skilled in the art can, based on the above disclosure and the examples below, utilize the present invention to its fullest extent. The following examples are to be construed as merely illustrative of how one skilled in the art can practice the invention, and are not limitative of the remainder of the disclosure in any way. Any publications cited in this disclosure are hereby incorporated by reference.

Example 1: Optoelectronic Device with Housing

Figure 2:
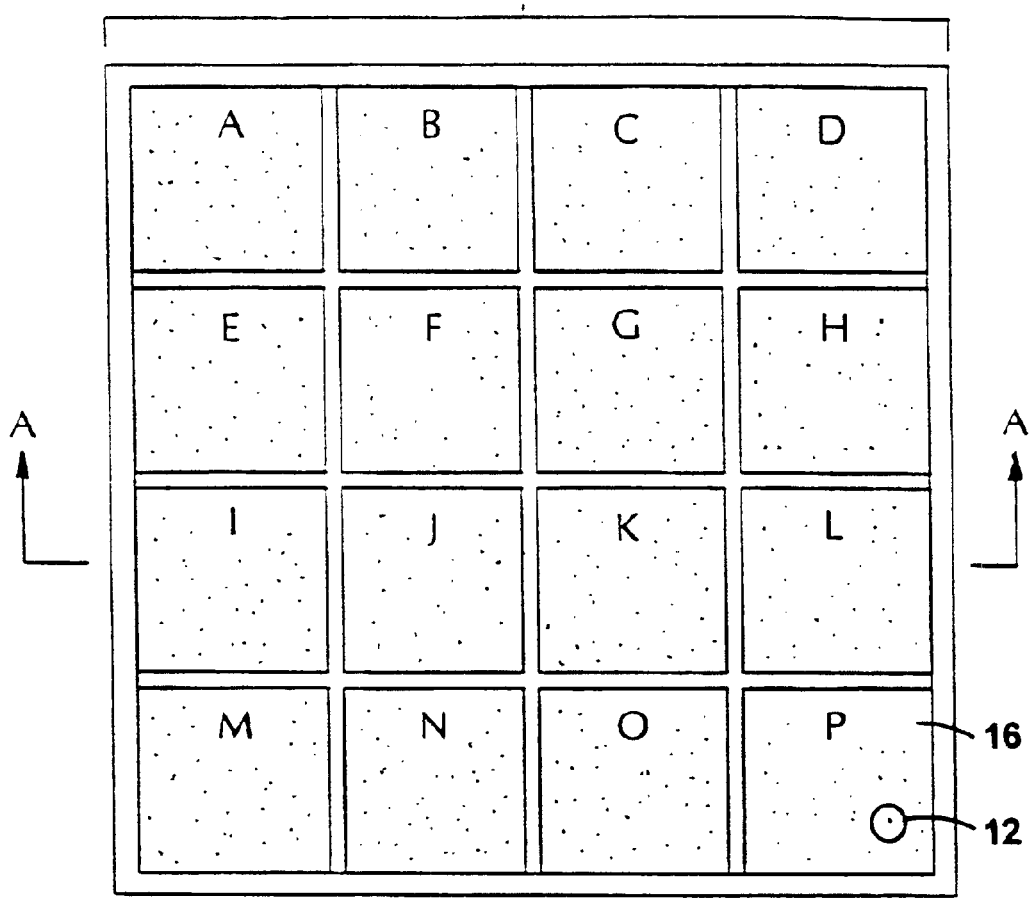
FIG. 2 is a top view of the device in FIG. 1 with the upper half of the housing removed.
Figure 3:
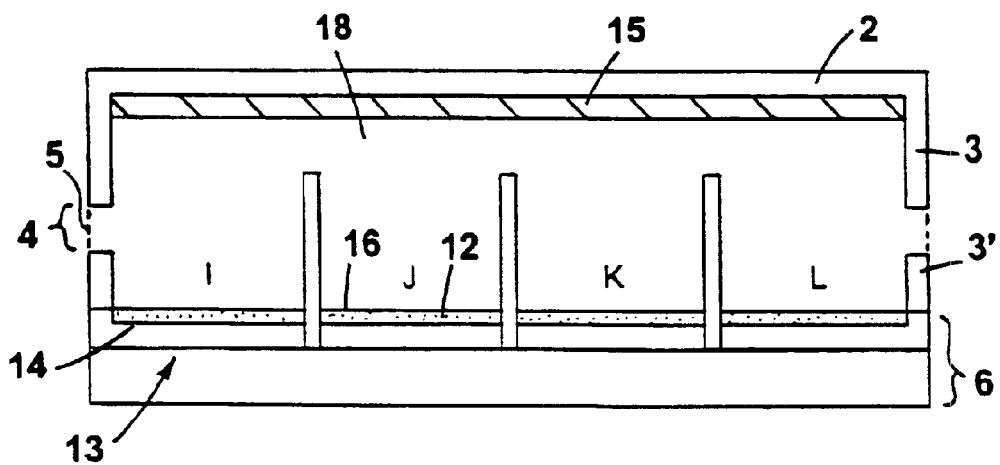
FIG. 3 is a cross-sectional view of the device taken along sectional line A—A of FIG. 2.

Referring to FIGS. 1–3, a device 1 for detecting multiple airborne antigens includes a housing 2 having an upper half 3 and a lower half 3' which together define an inner volume 18 (FIG. 3) of the device. When upper half 3 and lower half 3" are together (closed position), they also define an opening 4 through which the antigen to be detected enters the device 2. An antigen-permeable mesh 9 is positioned over the opening 4 to prevent the ingress of large particles which could interfere with proper functioning of the inner components. The upper half 3 of the housing 1 is attached to the lower half 3' by hinge 5, allowing the device 1 to be opened in a direction as indicated by arrow 8. Lower half 3' has an open bottom to receive an optical detector, here a CCD 6, which is discussed in greater detail below.

The top view of the device 1 when the upper half 3 of the housing 2 is removed is shown in FIG. 2. The device 1 includes an array 10 of sectors A–P, each sector includes liquid medium 16 containing cells 12 immersed therein. The liquid media 16 in the sectors are separated from each other by walls 17 to prevent intermixing of cells in each sector. The specific cells provided within the medium of a sector can all be the same type or may be specific to a particular antigen to be detected. In the latter case, the device 2 is capable of detecting a variety of different antigens. Although walls 17 are used as barriers in this embodiment, they are not always necessary. For instance, when the medium containing the cells are droplets of an aqueous solution, the droplets remain within the sector by water surface tension. Alternatively, the barriers can be edged grooves running between the sectors, in which case water surface tension at the edge of the groove will keep the droplets from intermixing. In another example, the cells are adhered to a surface and intermixing of the media in different sectors is not a problem.

Referring to FIG. 3, the optical detector 6 includes a detection surface 13. The optical detector has a glass covering 14 which is in contact with the liquid medium 16 containing cells 12. To increase photon detection efficiency, the device 1 includes a photon reflective layer 15 located on the inner surface of upper half 3 of the housing 2.

When the antigen to be detected binds to the antibodies on the surface of cells 12, calcium ions move into the cytosol as described in Wilson et al., J Exp Med 166:601–606 (1987). The increased cytosolic calcium concentration causes an emitter molecule to emit a photon, which is read by the optical detector 6. In one embodiment, each cell will have multiple copies of the emitter molecule and will emit multiple photons when activated. Optical detector 6 provides electrical signals representative of an image of array 10. The electrical signals are processed to indicate which of sectors of array 10 have detected the presence of an antigen. For example, the signals are received by a processor 20 which is connected to indicator 22 (e.g., a light or sound emitting device) of the presence of one or more of the antigens. In one embodiment, for example, indicator 22 includes lamps, each of which is associated with one of the sectors of array 10 and provides an indication of the presence of the antigen associated with that sector.

The arrangement of the optical detector 6 with respect to the media containing the cells can be varied. For example, the medium 16 could fill inner volume 18 between the glass covering 14 and the reflective layer 15, and the opening 4 is covered by a membrane or porous filter instead of mesh 9. In this case, the cells adhere to glass covering 14, rendering any walls 17 between sectors unnecessary. To facilitate adherence of the cells 12 to the glass covering 14, the glass can be coated with substances (e.g., poly-L-lysine or extracellular matrix proteins). In this variation of the device, an antigen in a liquid can be detected as long as the liquid containing the antigen contacts the membrane and diffuses through medium 16 to the cells 12. Alternatively, the housing 2 can be opened by pivoting upper half 3 and a liquid sample containing the antigen to be detected can be dropped into the medium 16.

The liquid medium 16 can contain nutrients, dissolved gases, cytokines, antibiotics (to inhibit contamination), or any other substance necessary for maintenance of the cells. Furthermore, the liquid medium can contain substances to aid the detection of calcium in activated cells (e.g., coelenterazine substrate or analogues thereof to recharge spent aequorin molecules or calcium-sensitive fluorescent substances). If necessary, the medium is maintained at a suitable temperature or pH.

Example 2: Use of B Cells in an Optoelectronic Sensor

The ability of B cells to emit photons in response to an extracellular signal was evaluated. K46J B cells were loaded with the calcium-sensitive fluorescent dye indo-1, stimulated by contacting the loaded cells with anti-IgM antibodies, and monitored for fluorescence as follows.

About five million cells were removed from their growth medium and resuspended in 1 ml Hank's Balanced Salt Solution (HBSS). One vial of indo-1 was mixed with 113 $\mu$l of fetal bovine serum (FBS) and 25 $\mu$l of pluronic F-127 detergent (20% in DMSO). The mixture was incubated at room temperature for five minutes. The FBS was necessary to solubilize the indo-1, even though when the indo-1 was added to the cells, the FBS was capable of temporarily activating the cells.

After the five minute incubation, 40 $\mu$l of 100 mM probenecid was added to the cells to improve loading. Then 15 $\mu$l of the indo-1 mixture as prepared above was added. The cells were incubated in the dark at 37□ C. for 25 minutes.

After the 25 minutes incubation, the cells were centrifuged and resuspended in 10 ml of HBSS and put on ice. One milliliter of the cell suspension was removed and placed in a FACS machine to measure the resting ratio of violet to green fluorescence from the indo-1. Less than 0.1% of the cells exhibited a steady-state fluorescence ratio of less than 600. Upon introduction of an appropriate amount of antimouse IgM antibody, greater than 58% of the cells exhibited a fluorescence ratio above 600 after about 100 seconds.

The results for the K46J cells indicated that a B cell can be stimulated to immobilize calcium by contacting that cell with a ligand that binds to antibodies on the cell surface.

The above procedure was repeated with the murine B cell line CH27, except that pervanadate was used to stimulate the cells, instead of an anti-IgM antibody. The CH27 exhibited a fluorescence response upon activation similar to that for the K46J cells. Taken together, these K46J and CH27 results confirmed the fast response that B cells can confer on an optoelectronic device incorporating them.

To further illustrate the use of B cells in the devices and methods of the invention, M12g3R murine B cells stably expressing an antibody specific for the hapten phosphorylcholine were evaluated. These cells also contained the emitter molecule aequorin, which was encoded by an expression plasmid introduced into the cells. About 1×10$^6$ of these cells were removed from their growth medium and resuspended in 1 ml of RPMI medium supplemented with 1% FBS. Twenty microliters of 1 mM coelenterazine in methanol, supplemented with glutathione was added to the cells. The mixture was incubated in the dark at room temperature for 1 to 4 hours. The solution contained glutathione in order to prevent oxidation of the coelenterazine. As discussed above, aequorin oxidizes coelenterazine when calcium levels rise in the cytoplasm, thereby emitting a photon.

After the room temperature incubation, the cells were resuspended in 2 ml of HEPES-buffered saline solution supplemented with 10 mM $CaCl_2$. The cell density was measured by placing a small drop of the mixture on a hemacytometer. Sixty microliters of cells were then placed in a clear plastic tube, and the tube placed inside a luminometer (i.e., a photomultiplier tube inside a light-tight box) to measure the background emission rate. The tube was then removed from the luminometer. Twenty microliters of phosphorylcholine-ovalbumin was then added to the tube, and the tube was place back into the luminometer for measurement. Within about 50 seconds after adding the phosphorylcholine-ovalbumin, the cells emitted more than 3×10$^5$ photons per second, which represents a peak emission rate that was 130 times the background emission rate.

The result from experiment immediately above confirmed that B cells containing an emitter molecule and having surface antibodies can be stimulated to emit photons in response to an antigen for which the antibodies are specific. Such cells are useful in the devices and methods of the invention.

To evaluate whether B cells of non-mammalian origin can be used, three catfish B cell lines (3B11, IG8, and C4-IE5) were loaded with indo-1, treated, and measured as described above for the CH27 cells. All three cell lines exhibited a substantial fluorescence ratio increase within about 100 seconds after adding pervanadate. Thus, B cells from cold-blooded vertebrates can be used in the devices and methods of the invention without the temperature controls sometimes required when cells from warm-blooded animals are used.

Example 3: Use of Non-B Cells in a Optoelectronic Sensor

To determine if cell types other than B cells were appropriate for use in an optoelectronic sensor, the murine fibroblast cell line BALB/c 3T3 was evaluated as follows.

About 7×10$^6$ 3T3 cells were removed from a confluent 10 cm$^2$ tissue culture plate by trypsinization. These cells were then treated as describe above for K46J cells, except that 100 $\mu$l of fetal bovine serum was used to stimulate calcium mobilization instead of an anti-IgM antibody. Before and after stimulation, the fibroblasts exhibited a fluorescence ratio similar to that seen for K46J cells as discussed above, indicating that fibroblasts, as well as B cells, are suitable for the devices and methods of the invention.

As a further illustration that fibroblasts can be used in place of B cells in the invention, an in vitro aequorin luminescence assay was performed on aequorin produced in 3T3 cells, and the result compared to that of aequorin produced in K46J cells. The in vitro aequorin assay is described in Button et al., Cell Calcium 14:663–671 (1993).

BALB/c 3T3 cells and K46J cells were transfected with a aequorin-expressing plasmid. Two to three days later, about 7×10$^6$ 3T3 cells were removed from a confluent 10 cm$^2$ tissue culture plate by trypsinization. A similar number of transfected K46J cells were also isolated. Both types of cells were washed with PBS and resuspended in 0.5 ml of a solution containing 30 mM Tris (pH 7.6) and 10 mM EDTA. The cell suspensions were frozen at −80° C. and thawed at room temperature three times to release the aequorin from the cells. The cells were then pelleted by centrifuging for 20 minutes at 4° C. and 14,000 RPM. The supernatant containing the aequorin was removed and analyzed.

Fifty microliters of the cell extracts were mixed with 50 $\mu$l of reaction buffer (30 mM Tris [pH 7.6], 10 mM EDTA, and 5% B-mercaptoethanol) and 10 $\mu$l of 11 $\mu$mM coelenterazine (Molecular Probes, Inc.). The tubes containing the mixtures were then wrapped in foil and incubated at room temperature for three hours.

At the end of the incubation, one of the tubes was read in a luminometer to obtain a background luminescence level. Then 100 $\mu$l of a 250 mM $CaCl_2$ solution was added to the extract, and the reading taken again within 30 seconds of adding calcium. The procedure was repeated for the other tube. The K46J extract exhibited a 18×increase in photon emission after the addition of calcium, while, surprisingly, the 3T3 extract indicated a 23×increase in photon emission after the addition of calcium. These results indicated that aequorin produced in fibroblasts, as well as B cells, are functional emitter molecules and can be used in the methods and devices of the invention.

Following the same procedure for the catfish B cells, another non-B cell, the catfish T cell line 28S.1, was tested for pervanadate activation. The results indicated that this cold-blooded non-B cell is also useful in the devices and methods of the invention.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

Furthermore, from the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

For example, the device of the invention can further include pumps, valves, fluid reservoirs, batteries, microprocessors, waste removal systems, and/or temperature control systems.

If desired, different cells binding to different parts of the sample antigen could be used to look for different identifying features on the same pathogen. On the one hand, this could be useful in situations where false positives are a problem, since multiple identifying features can be detected before declaring a positive identification. On the other hand, it could also be useful where false negatives are a problem, since even if a pathogen lacks one characteristic feature, it could still be detected on the basis of the other identifying feature.

Analysis of multiple antigens by the device can be performed in parallel for suitably high concentrations of antigens, and the sample containing the antigens can be introduced into a chamber containing cells sensitive to different antigens. However, serial analysis might be necessary for lower concentrations of antigens. The antigen sample can first be delivered to a cell specific for one antigen, then carried on to a different cell specific for another antigen. In one embodiment, a fluid channel winds back and forth over the surface of the optical detector, presenting the sample to one antigen-specific sector of cells at a time. Flow in the channel can be slow enough or can be periodically stopped in order to allow antigen-antibody binding. Serial detection is generally slower than parallel detection, so additional components of the device can be added to speed the detection process. Prior information about the sample could be used to reduce the number of antigen-specific types of cells to which the sample must be presented in series. For example, if the sample is known to contain a viral antigen, then it would only have to be presented to virus-specific cells. Also, the proximal sectors in the series could be designated for the detection of higher priority antigens (e.g., more rapidly acting pathogens).

The device can also be designed so that the cell populations can be easily replaced if they are killed or otherwise rendered ineffective. The support to which the cell lines are attached or in which the media is contained would be made removable. Extra supports containing the cell lines could be frozen or freeze-dried and then stored. After removing old cells from a sensor and inserting fresh cells, one could revive the device with the fresh cells.

After the sample has been examined by the cells, it can be flushed away (via the use of a reservoir of fresh medium and a pump, for example) from the cells, thereby preparing the device for the next sample and helping to prevent contamination or clogging of the device.

What is claimed is:

1. A device for detecting the presence of an antigen, comprising:

a cell having antibodies which are expressed on the surface of the cell and are specific for the antigen to be detected, wherein binding of the antigen to the antibodies results in an increase in calcium concentration in the cytosol of the cell, the cell further having an emitter molecule which, in response to the increased calcium concentration, emits a photon;

a liquid medium in which the cell is immersed, the liquid medium receiving the antigen to be detected; and an optical detector arranged for receiving the photon emitted from the cell.

2. The device of claim 1, wherein the optical detector is affixed to the liquid medium containing the cells.

3. The device of claim 1, wherein the optical detector is a charge-coupled device.

4. The device of claim 1, wherein the antibody is a chimeric antibody.

5. The device of claim 1, wherein the antibody is a single-chain antibody.

6. The device of claim 1, wherein the emitter molecule is aequorin.

7. A device for detecting the presence of two or more antigens, comprising:

an array containing a plurality of sectors, each sector containing a cell having antibodies which are expressed on the surface of the cell and are specific for the antigen to be detected, wherein binding of the antigen to the antibodies results in an increase in calcium concentration in the cytosol of the cell, the cell further having an emitter molecule which, in response to the increased calcium concentration in the cytosol, emits a photon;

liquid media in which the cell of each sector is immersed; and an optical detector arranged for receiving the photon emitted from the cell;

wherein each sector contains a cell having antibodies specific to a different antigen.

8. The device of claim 7, wherein the optical detector is affixed to the liquid medium containing the cells.

9. The device of claim 7, wherein the optical detector is a charge-coupled device.

10. The device of claim 7, wherein the antibody is a chimeric antibody.

11. The device of claim 7, wherein the antibody is a single-chain antibody.

12. The device of claim 7, wherein the emitter molecule is aequorin.

13. The device of claim 7, wherein the liquid media receives the antigen to be detected.

* * * * *

UNITED STATES PATENT AND TRADEMARK OFFICE
CERTIFICATE OF CORRECTION

PATENT NO. : 6,800,448 B2
DATED : October 5, 2004
INVENTOR(S) : Todd H. Rider and Laura Smith It is certified that error appears in the above-identified patent and that said Letters Patent is hereby corrected as shown below:

<u>Column 1,</u>
Line 9, before the title "BACKGROUND OF THE INVENTION" please insert the following paragraph:

-- GOVERNMENT SUPPORT

The invention was supported in whole, or in part, by Contract Number F19628-95-C-0002 awarded by the U.S. Air Force. The Government has certain rights in the invention. --

Signed and Sealed this

Eighth Day of March, 2005

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 6,800,448 B2 | Page 1 of 1 |
| APPLICATION NO. | : 09/848811 | |
| DATED | : October 5, 2004 | |
| INVENTOR(S) | : Todd H. Rider and Laura Smith | |

It is certified that error appears in the above-identified patent and that said Letters Patent is hereby corrected as shown below:

At column 1, line 9, before the title "BACKGROUND OF THE INVENTION" please insert the following paragraph:

--This invention was made with Government support under Contract No. F19628-95-C-0002 awarded by the Air Force. The Government has certain rights in the invention.--

Signed and Sealed this
Eighth Day of March, 2016

Michelle K. Lee
*Director of the United States Patent and Trademark Office*